US008586044B2

(12) United States Patent
Thumbikat et al.

(10) Patent No.: US 8,586,044 B2
(45) Date of Patent: Nov. 19, 2013

(54) TREATMENT OF CHRONIC PELVIC PAIN SYNDROME

(75) Inventors: Praveen Thumbikat, Skokie, IL (US); Anthony J. Schaeffer, Hinsdale, IL (US); Joseph Done, Morton Grove, IL (US); David J. Klumpp, Chicago, IL (US); Charles Rudick, Chicago, IL (US)

(73) Assignee: Northwestern University, Evanston, IL (US)

( * ) Notice: Subject to any disclaimer, the term of this patent is extended or adjusted under 35 U.S.C. 154(b) by 165 days.

(21) Appl. No.: 13/118,156

(22) Filed: May 27, 2011

(65) Prior Publication Data

US 2011/0293631 A1 Dec. 1, 2011

Related U.S. Application Data

(60) Provisional application No. 61/349,282, filed on May 28, 2010, provisional application No. 61/349,277, filed on May 28, 2010.

(51) Int. Cl.
*A61K 39/395* (2006.01)
*C07K 16/24* (2006.01)
*C12P 21/08* (2006.01)

(52) U.S. Cl.
USPC .......... 424/145.1; 424/130.1; 424/141.1; 530/387.1; 530/388.1; 530/388.23

(58) Field of Classification Search
None
See application file for complete search history.

(56) References Cited

U.S. PATENT DOCUMENTS

| 6,180,355 B1 | 1/2001 | Alexander et al. |
| 2005/0277140 A1 | 12/2005 | Schaeffer et al. |

OTHER PUBLICATIONS

Alexander et al., 1996, "Chronic prostatitis: results of an Internet survey", Urology 48: 568-574.
Bahnson, 1991, "Elevation of prostate specific antigen from bacillus Calmette-Guerin-induced granulomatous prostatitis", J. Urology, 146: 1368-69.
Dhundee et al., 1991, "An immunohistological study of granulomatous prostatitis", Histopathology 18: 435-41.
Dower et al., 1985, "Detection and characterization of high affinity plasma membrane receptors for human interleukin 1", J Exp Med, 162: 501-15.
Kohnen et al., 1979, "Patterns of inflammation in prostatic hyperplasia: a histologic and bacteriologic study", J. Urology, 121: 755-60.
Meares et al., 1968, "Bacteriologic localization patterns in bacterial prostatitis and urethritis", Invest Urol, 5: 492.
Mosmann, 1992, "T lymphocyte subsets, cytokines, and effector functionsb", Ann NY Acad Sci, 664: 89-92.
Nadler et al., 2000, "IL-1beta and TNF-alpha in prostatic secretions are indicators in the evaluation of men with chronic prostatitis", J Urology, 164: 214-218.
Steiner et al., 1994, "Phenotype and function of peripheral and prostatic lymphocytes in patients with benign prostatic hyperplasia", J. Urology 151: 480-84.
Stillwell et al., 1987, "The clinical spectrum of granulomatous prostatitis: a report of 200 cases", J. Urology, 138: 320-23.
Theyer et al., 1992, "Phenotypic characterization of infiltrating leukocytes in benign prostatic hyperplasia", Lab Invest, 66: 96-107.
Zisman et al., 1995, "Autoantibodies to prostate specific antigen in patients with benign prostatic hyperplasia", J. Urology, 154: 1052-55.

*Primary Examiner* — Christine J Saoud
*Assistant Examiner* — Jon M Lockard
(74) *Attorney, Agent, or Firm* — Casimir Jones SC

(57) ABSTRACT

The present invention provides compositions and methods for detection, diagnosis, treatment and/or prevention of chronic pelvic pain syndrome. In particular, the present invention provides biomarkers of chronic pelvic pain syndrome (e.g., mast cell markers (e.g., tryptase)), and/or inhibition of mast cell function (e.g. inhibition of MCP-1 and/or MIP-1α) to treat or prevent chronic pelvic pain syndrome.

9 Claims, 14 Drawing Sheets

Figure 11

| Routes | Dosing/route |
|---|---|
| Oral | 0.5 mg/kg Cromolyn Sodium (CS) |
| Intraperitoneal | 1.0 mg/kg CS |
| Intravenous | 0.5 mg/kg CS + 2.5 mg/kg Cetirizine (H1) |
| | 1.0 mg/kg CS + 2.5 mg/kg H1 |

TREATMENT OF CHRONIC PELVIC PAIN SYNDROME

This application claims priority to U.S. Provisional Patent Application Ser. No. 61/349,282, filed May 28, 2010, and U.S. Provisional Patent Application Ser. No. 61/349,277, filed May 28, 2010, both of which are herein incorporated by reference in their entireties.

STATEMENT REGARDING FEDERALLY SPONSORED RESEARCH OR DEVELOPMENT

This invention was made with government support under Grant No. 1K01DK079019-01A2 awarded by the National Institutes of Health, National Institute of Diabetes and Digestive and Kidney Diseases. The government has certain rights in the invention.

FIELD OF THE INVENTION

The present invention provides compositions and methods for detection, diagnosis, treatment and/or prevention of chronic pelvic pain syndrome. In particular, the present invention provides biomarkers of chronic pelvic pain syndrome (e.g., mast cell markers (e.g., tryptase)), and/or inhibition of mast cell function (e.g. inhibition of MCP-1 and/or MIP-1α) to treat or prevent chronic pelvic pain syndrome.

BACKGROUND OF THE INVENTION

Chronic prostatitis/chronic pelvic pain syndrome (collectively referred to herein as CPPS) is a syndrome of undetermined etiology occurring in men. CPPS is the third of four subgroups of prostatitis recognized by the National Institutes of Health. Category I encompasses acute bacterial prostatitis, and Category II covers chronic bacterial infection. Category III, CPPS, includes all remaining prostatitis syndromes, and is subdivided into IIIa (inflammatory) and IIIb (non-inflammatory). These sub-categories can be distinguished by the presence of leukocytosis in expressed prostatic secretions or sediment in a post-massage urine sample. Category IV represents asymptomatic prostatitis, which often is associated with benign prostate hyperplasia.

Prostatitis is extraordinarily common, resulting in approximately 2 million office visits to primary care physicians and urologists in the United States annually (1997 American Urological Association Annual Meeting, National Ambulatory Medical Care Survey, National Center for Health Statistics, 1990 to 1994). Patients with CPPS suffer from chronic, episodic pain in the perineum or pelvic region, irritative and obstructive voiding symptoms, and adverse effects upon sexual function (Alexander et al., Urology 48:568-574 (1996)). Men with chronic prostatitis often require repeated physician visits. Medical expenditures relating to CPPD are conservatively estimated to exceed half a billion dollars annually.

While an enormous number of patients seek the care of a physician because of prostatitis-like symptoms, almost nothing is known about diagnostic criteria, etiology, or objective signs for CPPS. Pain in the pelvic region is the most frequently reported and the most severe symptom in patients with CPPS (Alexander et al., Urology 48:568-74 (1996)). It was because of these observations and the paucity of objective criteria for defining the disease, which the National Institute of Diabetes and Digestive and Kidney Diseases working group in prostatitis suggested that the disease be named Chronic Pelvic Pain Syndrome.

One reason for the present state of confusion regarding CPPS is the similarity of CPPS symptoms to the symptoms of bacterial prostatitis. Only about 5 to 10% of patients whose symptoms are consistent with bacterial prostatitis are shown to have infection in the prostate gland (Weidner et al., Infection 19:S109-S190 (1991)). The misdiagnosis of CPPS as infectious prostatitis commonly results in unnecessary treatment with multiple courses of antibiotics at burdensome costs to patients and to the health care system with no demonstrated benefit to patients.

Much effort has been expended to identify an organism underlying the cause of CPPS but no clear consensus has emerged identifying any such organism as the causative agent. Additionally, some men with CPPS have evidence of inflammation of the prostate. While the cellular and cytokine mediators involved in the inflammatory process have been increasingly clarified in the immunologic literature, few studies have investigated the immunobiology of the prostate gland to determine whether CPPS might arise from an auto-immune-like condition.

SUMMARY OF THE INVENTION

In some embodiments, the present invention provides compositions and methods for treatment and/or prevention of chronic pelvic pain syndrome. In particular, the present invention provides compositions and methods for inhibition of mast cell function to treat or prevent chronic pelvic pain syndrome. In some embodiments, chronic pelvic pain syndrome is treated or prevented by inhibition of mast cell function and one or more additional therapies (e.g. inhibition of MCP-1 and MIP-1α).

In some embodiments, the present invention provides a method for treating and/or preventing chronic pelvic pain syndrome in a subject, comprising administering therapeutic composition comprising a therapeutically effective amount of an inhibitor of mast cell function to the subject. In some embodiments, the therapeutic composition further comprises an inhibitor of MCP-1 and/or MIP-1α. In some embodiments, the therapeutic composition comprises two or more inhibitors of MCP-1 and/or MIP-1α. In some embodiments, the inhibitor of MCP-1 and/or MIP-1α comprises an antisense olgionucteotide, genetic therapy, or anti-chemokine therapy. In some embodiments, the inhibitor of mast cell function comprises a mast cell stabilizer and/or histamine receptor antagonist. In some embodiments, the mast cell stabilizer comprises sodium, lodoxamide, nedocromil, and/or derivatives thereof. In some embodiments, the histamine receptor antagonist comprises a histamine receptor 1 antagonist. In some embodiments, the histamine receptor 1 antagonist comprises: clemastine, diphenhydramine, doxylamine, loratadine, desloratadine, fexofenadine, pheniramine, cetirizine, ebastine, promethazine, chlorpheniramine, levocetirizine, quetiapine, meclizine, dimenhydrinate, and/or derivatives thereof. In some embodiments, the histamine receptor antagonist comprises a histamine receptor 2 antagonist. In some embodiments, the histamine receptor 1 antagonist comprises: cimetidine, famotidine, ranitidine, nizatidine, roxatidine, lafutidine, and derivatives thereof.

In some embodiments, the present invention provides a method for treating and/or preventing chronic pelvic pain syndrome in a subject, comprising co-administering an inhibitor of mast cell function, and one or more inhibitors of MCP-1 or MIP-1α. In some embodiments, the one or more inhibitors of MCP-1 or MIP-1α comprise inhibitors of MCP-1 and MIP-1α. In some embodiments, the one or more inhibitors of MCP-1 or MIP-1α comprise an antisense olgionucteotide, genetic therapy, or anti-chemokine therapy. In some embodiments, the inhibitor of mast cell function comprises a mast cell stabilizer, inhibitor of degranulation, or histamine receptor antagonist. In some embodiments, the mast cell stabilizer comprises sodium, lodoxamide, nedocromil, and/or derivatives thereof. In some embodiments, the histamine receptor antagonist comprises a histamine receptor 1 antagonist. In some embodiments, the histamine receptor 1 antagonist comprises: clemastine, diphenhydramine, doxylamine, loratadine, desloratadine, fexofenadine, pheniramine, cetirizine, ebastine, promethazine, chlorpheniramine, levocetirizine, quetiapine, meclizine, dimenhydrinate, and/or derivatives thereof. In some embodiments, the histamine receptor antagonist comprises a histamine receptor 2 antagonist. In some embodiments, the histamine receptor 1 antagonist comprises: cimetidine, famotidine, ranitidine, nizatidine, roxatidine, lafutidine, and derivatives thereof.

In some embodiments, the present invention provides a composition for the treatment or prevention of CPPS, comprising: (a) an inhibitor of mast cell function, and (b) an inhibitor of a CPPS biomarker. In some embodiments, the inhibitor of mast cell function comprises a mast cell stabilizer, inhibitor of degranulation, or histamine receptor antagonist. In some embodiments, the mast cell stabilizer comprises sodium, lodoxamide, nedocromil, and/or derivatives thereof. In some embodiments, the histamine receptor antagonist comprises a histamine receptor 1 antagonist. In some embodiments, the histamine receptor 1 antagonist comprises: clemastine, diphenhydramine, doxylamine, loratadine, desloratadine, fexofenadine, pheniramine, cetirizine, ebastine, promethazine, chlorpheniramine, levocetirizine, quetiapine, meclizine, dimenhydrinate, and/or derivatives thereof. In some embodiments, the present invention comprises two or more inhibitors of biomarkers of CPPS. In some embodiments, the biomarkers of CPPS are selected from MCP-1 and MIP-1α. In some embodiments, the biomarkers of CPPS comprise inhibitors of MIP-1α and MCP-1.

In some embodiments, the present invention provides biomarkers of chronic pelvic pain syndrome for use in diagnosis, drug screening, therapy monitoring, research and therapeutic applications. In particular, the present invention provides mast cell markers (e.g., tryptase) as biomarkers of chronic pelvic pain syndrome.

Accordingly, in some embodiments, the present invention provides a method for detecting chronic pelvic pain syndrome in a subject, comprising providing a sample from a subject; and detecting the expression of a mast cell-specific marker (e.g., tryptase) in the sample. Any mast cell-specific marker or a combination of markers specific for mast cells (a mast cell fingerprint) may be used. In some embodiments, one or more proteins, peptides, or nucleic acid molecules (e.g., DNA, RNA) is detected or quantified. Embodiments of the invention are illustrated below using mast cell tryptase as an exemplary marker. It should be understood that in some embodiments, similar methods, kits, compositions, and the like may be employed with other mast-specific markers.

In some embodiments, detecting the expression of mast cell tryptase comprises detecting the presence of mast cell tryptase mRNA. In some embodiments, detecting expression of mast cell tryptase comprises exposing the mast cell tryptase mRNA to a nucleic acid probe complementary to the mast cell tryptase mRNA. In some embodiments, detecting expression of mast cell tryptase comprises detecting the presence of a mast cell tryptase polypeptide. In some embodiments, detecting the presence of a mast cell tryptase polypeptide comprises exposing the mast cell tryptase polypeptide to an antibody specific to the mast cell tryptase polypeptide and detecting the binding of the antibody to the mast cell tryptase polypeptide. In some embodiments, the subject comprises a human subject. In some embodiments, the sample comprises semen, seminal fluid, and/or expressed prostatic secretions.

The present invention also provides a method for selecting a therapeutic course of action, comprising providing a sample from a subject; detecting the expression of mast cell tryptase in the sample; and treating the subject based upon the expression of mast cell tryptase.

The present invention provides a kit for characterizing CPPS in a subject, comprising a reagent capable of specifically detecting the presence or absence of expression of mast cell tryptase; and, optionally, instructions for using the kit for characterizing pain in the subject. In some embodiments, the reagent comprises a nucleic acid probe complementary to a mast cell tryptase mRNA. In some embodiments, the reagent comprises an antibody that specifically binds to a mast cell tryptase polypeptide.

The present invention also provides a method of screening compounds, comprising providing a sample; and one or more test compounds; and contacting the sample with the test compound; and detecting a change in mast cell tryptase expression in the sample in the presence of the test compound relative to the absence of the test compound. In some embodiments, the detecting comprises detecting mast cell tryptase mRNA. In some embodiments, the detecting comprises detecting mast cell tryptase polypeptide. In some embodiments, the cell is in vitro or in vivo. In some embodiments, the test compound comprises an antisense compound. In some embodiments, the test compound comprises a small molecule drug.

In some embodiments, the present invention provides a method for detecting chronic pelvic pain syndrome in a subject, comprising providing a sample from a subject; and detecting the expression of mast cell tryptase, along with one or more additional biomarkers of chronic pelvic pain syndrome, in the sample. In some embodiments, additional biomarkers of chronic pelvic pain syndrome comprise MIP-1α and/or MCP-1.

In some embodiments, the present invention provides a kit for characterizing CPPS in a subject, comprising a reagent capable of specifically detecting the presence or absence of expression of mast cell tryptase and one or more additional biomarkers of chronic pelvic pain syndrome. In some embodiments, additional biomarkers of chronic pelvic pain syndrome comprise MIP-1α and/or MCP-1.

The present invention also provides a method of screening compounds, comprising providing a sample; and one or more test compounds; and contacting the sample with the test compound; and detecting a change in expression of mast cell tryptase and one or more additional biomarkers of chronic pelvic pain syndrome in the sample in the presence of the test compound relative to the absence of the test compound. In some embodiments, additional biomarkers of chronic pelvic pain syndrome comprise MIP-1α and/or MCP-1.

The present invention also provides a panel of markers for detection of CPPS in a subject, comprising mast cell tryptase, and one or more additional markers of CPPS. In some embodiments, additional markers of CPPS comprise MIP-1α and/or MCP-1.

DESCRIPTION OF THE DRAWINGS

FIG. 11 shows a chart of treatment groups assessed. One group was given oral administered cromolyn sodium at 0.5 mg/kg. A second group was given intraperitoneal administered cromolyn sodium at 1.0 mg/kg. Two additional groups were given intravenous administered cromolyn sodium at 0.5 mg/kg in combination with Cetirizine (H1) 2.5 mg/kg, or cromolyn sodium at 1.0 mg/kg in combination with Cetirizine (H1) 2.5 mg/kg.

DEFINITIONS

Figure 1:
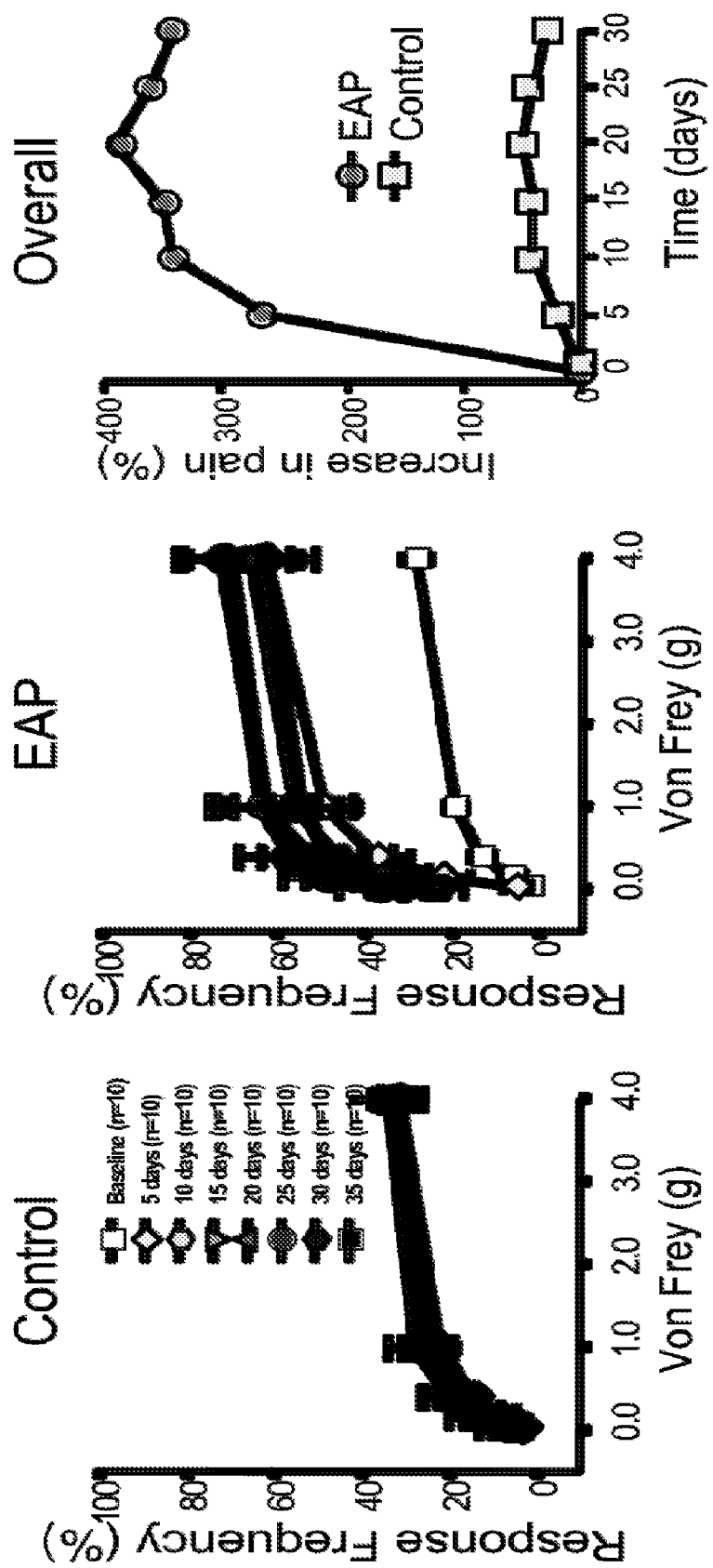
FIG. 1 shows the EAP induces chronic pelvic pain in male NOD mice. Mice were assessed for tactile allodynia with von Frey filaments before and after immunization. Sham-injected male NOD mice received adjuvant injection while experimental NOD mice were injected with antigen. ANOVA exhibited significantly increased responses at all filaments tested in PAg-treated mice at days 10-30, with no significant differences in baseline between controls and PAg-treated mice. EAP induced 300-400% increase in pain compared to controls.

To facilitate an understanding of the present invention, a number of terms and phrases are defined below:

The term "epitope" as used herein refers to that portion of an antigen that makes contact with a particular antibody.

As used herein, the term "subject" refers to any animal (e.g., a mammal), including, but not limited to, humans, non-human primates, rodents, and the like, which is to be the recipient of a particular treatment or subject to various tests (e.g., diagnostic tests) that may be provided by the present invention. Typically, the terms "subject" and "patient" are used interchangeably herein in reference to a human subject.

As used herein, the term "subject suspected of having CPPS" refers to a subject that presents one or more symptoms indicative of chronic pelvic pain syndrome (CPPS) or is being screened for CPPS (e.g., during a routine physical). A subject suspected of having CPPS may also have one or more risk factors. A subject suspected of having CPPS has generally not been tested for CPPS. However, a "subject suspected of having CPPS" encompasses an individual who has received an initial diagnosis but for whom the nature of the CPPS is not known. The term further includes people who once had CPPS.

As used herein, the term "subject at risk for CPPS" refers to a subject with one or more risk factors for developing CPPS.

As used herein, the term "characterizing CPPS in a subject" refers to the identification of one or more properties of CPPS in a subject.

The terms "test compound" and "candidate compound" refer to any chemical entity, pharmaceutical, drug, and the like that is a candidate for use to treat or prevent a disease, illness, sickness, or disorder of bodily function (e.g., CPPS). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include, among other things, body fluids (e.g., semen), blood products (e.g., plasma, serum and the like), and their component parts (e.g., expressed prostatic secretions, termed "ESPs" herein, seminal plasma or seminal fluid). Environmental samples include environmental material such as surface matter, soil, water, and industrial samples. Such examples are not however to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "CPPS marker" or "CPPS marker genes" refers to a biomarker (e.g., gene) whose presence, absence, concentration, and/or expression level (e.g., as detected by mRNA or protein expression), alone or in combination with other markers, is correlated with CPPS or prognosis of CPPS. The correlation may relate to either an increased or decreased expression of the gene. For example, the expression of the gene may be indicative of CPPS, or reduced level of expression of the gene may be correlated with response to therapy for CPPS in a CPPS patient.

As used herein, the term "a reagent that specifically detects expression levels" refers to reagents used to detect the expression of one or more genes or proteins (e.g., including but not limited to, the CPPS markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-CPPS control" refers to measuring the level of expression of a gene (e.g., the level of mRNA or protein) relative to the level in a non-CPPS control sample. Gene expression can be measured using any suitable method, including but not limited to, those described herein.

As used herein, the term "detecting a change in gene expression (e.g., mast cell tryptase) in a sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "instructions for using said kit for detecting CPPS in said subject" includes instructions for using the reagents contained in the kit for the detection and characterization of CPPS in a sample from a subject.

As used herein, the term "CPPS expression profile map" refers to a presentation of expression levels of genes in a sample (e.g., prostate tissue or seminal fluid) The map may be presented as a graphical representation (e.g., on paper or on a computer screen), a physical representation (e.g., a gel or array) or a digital representation stored in computer memory. Each map corresponds to a particular type of sample and thus provides a template for comparison to a patient sample.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of CPPS (e.g., as determined by the diagnostic methods of the present invention) on a subject's future health (e.g., likelihood of responding to therapy).

As used herein, the term "subject diagnosed with a CPPS" refers to a subject who has been tested and found to have CPPS. The CPPS may be diagnosed using any suitable method, including but not limited to, the diagnostic methods of the present invention.

As used herein, the term "initial diagnosis" refers to results of initial CPPS diagnosis (e.g. the presence or absence of CPPS).

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "co-administration" refers to the administration of two or more compositions to a subject. The compositions may be administered to treat the same or different diseases, disorders, and/or conditions. The compositions may be administered by the same route or different routes of administration (e.g. oral, parenateral, topical, intervenous, transmucosal, and/or inhalation routes). The compositions may be administered simultaneously or at different times. The compositions may be administered simultaneously, but formulated for release at different times or in different regions of the subject. The compositions may target the same or different pathways within the subject.

DETAILED DESCRIPTION OF THE INVENTION

Prostatitis is the most frequent urologic diagnosis in men under the age of 50, accounting for 8% of all office visits to urologists. The majority of prostatitis cases are classified as chronic pelvic pain syndrome (CPPS, NIH Category III). It is subclassified into categories IIIA (inflammatory) and IIIB (non-inflammatory). While various mechanisms including immunologic dysfunction, infectious, and neurologic dysfunction have been cited in the development of the syndrome, the etiology and pathogenesis of CPPS is poorly understood. Effective treatment for the CPPS remains uncertain. Factors complicating the management of this condition include its multifactorial pathogenesis, lack of a gold standard for diagnostic testing, and the methodologic limitations of many treatment studies.

There is a substantial body of evidence that demonstrates the occurrence of immunological activity within the prostate gland. However, the nature and cause of this activity, and whether it is detrimental to the host, has not been determined. Inflammatory infiltrates in the prostate are very common. In one study of 162 cases of surgically resected prostatic tissue, 98% possessed inflammatory infiltrates (Kohnen et al., J. Urology 121:755-60 (1979)). The infiltrating cells consisted of monocytes and activated T and B lymphocytes (Theyer et al., Lab Invest. 66:96-107 (1992); Steiner et al., J. Urology 151:480-84 (1994)).

A rare form of prostatic inflammation, granulomatous prostatitis, has been characterized, although the etiology of the inflammation is also unknown. One major theory about the disease, however, is that it represents an immune reaction against self prostatic proteins induced by infection or manipulation of the gland by previous biopsy or surgical procedure (Stillwell et al., J. Urology 138:320-23 (1987); Dhundee et al., Histopathology 18:435-41 (1991)).

The disease is also observed after instillation of Bacillus Calmette-Guerin (BCG) into the bladder as a treatment for superficial bladder cancer (Bahnson, J. Urology 146:1368-69 (1991)).

Recent observations about the existence of subsets of CD4+ T cells has yielded fundamental information about immune responses in humans. CD4+ T cells can be separated into subsets based upon the patterns of cytokines they secrete (Mosmann, Ann NY Acad. Sci. 664:89-92 (1992)). CD4+ T cells that secrete, among other cytokines, IFN-γ and IL-2 are called T helper 1 (Th1) cells. Th1 cells mediate cellular immunity, such as delayed hypersensitivity responses. CD4+ T cells that secrete, among other cytokines, IL-4 and IL-10 are termed T helper 2 (Th2). Th2 cells are associated with antibody production and allergy. Immune responses mediated by Th1 and Th2 cells can be characterized by the local cytokine environment during an immune response.

Zisman et al. found IgG anti-PSA antibody titers to be higher in the serum of men with benign prostate hyperplasia (BPH) compared to controls (Zisman et al., J. Urology 154: 1052-55 (1995)). However, of 17 men with chronic prostatitis, no discernable difference was found in mean antibody titer as compared to controls. Zisman et al. speculate that an immunologic mechanism may play a role in the symptomatology of BPH. An alternative explanation is that a Th1 type of response may be occurring in patients with chronic prostatitis/chronic pelvic pain syndrome. In this event, no antibody response would be expected.

Nonbacterial prostatitis, recently defined as chronic pelvic pain syndrome (CPPS), is characterized by pelvic or perineal pain and is associated with prostatic inflammation (Chronic Prostatitis Workshop, National Institute of Health, Bethesda, Md., Dec. 7-8, 1995). CPPS is the most common urologic diagnosis in men less than 50 years of age, yet little is known about its etiology and treatment. Nonbacterial prostatitis has been traditionally defined by the identification of white blood cells (WBC) in expressed prostatic secretions (EPS) in the absence of bacterial infection (Meares et al., Invest Urol, 5: 492 (1968)). Thus, the identification of inflammatory mediators such as cytokines in EPS are contemplated to be useful in the classification of men with CPPS.

Cytokines are small protein molecules produced and used by immune and inflammatory cells to communicate, control the environment, and regulate local and systemic events of the immune response. Most cytokines are produced and released locally and mediate their effects at the site of injury, infection or inflammation by autocrine and paracrine mechanisms. A number of cytokines regulate inflammation, including interleukin-1 (IL-1) and tumor necrosis factor alpha (TNF-α). IL-1α and IL-1β, collectively termed IL-1, share only 26% homology but act via the same high affinity receptor (Dower et al., J Exp Med, 162: 501 (1985)). IL-1 has a wide range of target cells and acts to promote antigen specific immune responses, inflammation and tissue repair. TNF-α is synthesized by cells of the monocyte/macrophage lineage. Synthesis of TNF-α is induced by bacterial proteins, viruses and fungal antigens, making its role in infection and inflammation prominent. To better understand the nature of CPPS, the inventors evaluated the EPS of men with no urologic disease, Benign Prostatic Hyperplasia (BPH), CPPS and asymptomatic inflammatory prostatitis (AIP) for the presence of leukocytes and cytokines.

Previous studies by the inventors demonstrated that the cytokines interleukin-1 (IL-1), tumor necrosis factor-α (TNF-α), IL-8, and epithelial neutrophil activating peptide-78 were significantly higher in samples from men with IIIa, but not IIIb, CPPS compared to controls (See, e.g., Nadler et al., Journal of Urology, 164: 214-218 (2000)).

The present invention provides compositions and methods for prostatic disease (e.g., CPPS) diagnostics, including but not limited to, CPPS markers (e.g., mast cell markers). Accordingly, the present invention provides methods of characterizing samples (e.g., expressed prostatic secretions or semen), kits for the detection of markers, as well as drug screening and therapeutic applications. Further, the present invention provides compositions and methods for treatment and/or prevention of CPPS.

I. Detection/Diagnosis/Characterization

The present invention provides markers whose expression is specifically altered in prostatic disease. Such markers find use in the diagnosis, detection, and/or characterization of prostatic disease (e.g., CPPS).

A. Identification of Markers

Experiments conducted during development of embodiments of the present invention demonstrate that mast cell tryptase is present, and significantly elevated, in samples of men with CPPS.

Thus, in some embodiments, the present invention provides biologic markers for CPPS (e.g., markers that identify mast cells). In some embodiments, detecting the levels of mast cell markers in a sample permits diagnosis of or increased likelihood of prostatic disease (e.g., CPPS). In some embodiments, biomarkers of the present invention (e.g., mast cell tryptase) are used in order to further understand and characterize the etiology and pathogenesis of CPPS.

In some embodiments, presence of or levels of mast cell tryptase is detected in a sample. In some embodiments, samples are obtained from a subject (e.g., a patient), and include, but are not limited to, fluids, solids, tissues, and gases. In some embodiments, biological samples include, among other things, body fluids (e.g., semen or saliva), blood products (e.g., plasma, serum and the like), and their component parts. In preferred embodiments, samples include expressed prostatic secretions, seminal plasma and/or seminal fluid.

In some embodiments, the present invention provides detection of and/or measurement of mast cell tryptase as indicative of the presence or absence of prostate disease (e.g., CPPS) in a subject. In some embodiments, the present invention provides diagnosis, characterization (e.g. identification of subtype), identification, etc. of CPPS based on detection of mast cell tryptase. In some embodiments, the present invention provides diagnosis, characterization (e.g. identification of subtype), identification, etc. of CPPS based on detection of mast cell tryptase above a threshold level (e.g. above a defined concentration in a body fluid). In some embodiments, patients are categorized (e.g., as IIIa and IIIb) and therapies or other interventions selected according to the levels of mast cell tryptase detected. It is contemplated that, in some embodiments, subjects with certain levels of mast cell tryptase (e.g., elevated levels), as compared to controls, are classified as having prostatic disease (e.g., CPPS).

In some embodiments, mast cell tryptase is detected in conjunction with other biomarkers (e.g. chemokines (e.g., MIP-1α and MCP-1)). In some embodiments, mast cell tryptase is detected individually (e.g. without other biomarkers). It is contemplated that, according to experiments conducted during the development of the present invention, that detection of mast cell tryptase enhances the sensitivity of predicting disease (e.g., prostatic) and classifying disease (e.g., CPPS) over other methods known to those in the art. In some embodiments, detection of mast cell tryptase, is used in combination with detection of other markers (e.g. chemokines/cytokines), including, but not limited to MIP-1α, MCP-1, GMCSF, IL-1, IL-2, IL-3, IL-4, IL-5, IL-6, IL-7, IL-8, IL-9, IL-10, IL-11, IL-12, IL-13, IL-14, IL-15, α-inteferon, γ-interferon, GRO-α, RENTES, fractalkine, VEGF, and TNF, in order to detect or classify disease (e.g., CPPS and CPSI, respectively). In some embodiments, detection of mast cell tryptase, is used in combination with symptom identification to detect or classify disease (e.g., CPPS and CPSI, etc.).

B. Detection of Markers

In some embodiments, the present invention provides methods for detection of expression of prostatic disease (e.g., CPPS markers). In preferred embodiments, expression is measured directly (e.g., at the RNA or protein level). In some embodiments, expression is detected in samples (e.g., semen, seminal fluid, seminal plasma or expressed prostatic secretions). In other embodiments, expression is detected in bodily fluids (e.g., including but not limited to, plasma, serum, whole blood, mucus, and urine). The present invention further provides panels and kits for the detection of markers. In preferred embodiments, the presence of a CPPS marker is used to provide a prognosis to a subject. For example, the detection of mast cell tryptase in samples is indicative of CPPS. The information provided is also used to direct the course of treatment. For example, if a subject is found to have a marker (e.g., as described herein) indicative of the presence of CPPS, therapies can be started immediately in place of or in addition to other treatments that would have otherwise been used. In addition, if a subject is found to have a CPPS that is not responsive to other therapies, the expense and inconvenience of such therapies can be avoided.

The present invention is not limited mast cell tryptase as a marker. Any suitable marker that correlates with CPPS may be utilized, including but not limited to, MIP-1α, MCP-1, GMCSF, IL-1, IL-2, IL-3, IL-4, IL-5, IL-6, IL-7, IL-8, IL-9, IL-10, IL-11, IL-12, IL-13, IL-14, IL-15, α-inteferon, γ-interferon, GRO-α, RENTES, fractalkine, VEGF, and TNF. Additional markers are also contemplated to be within the scope of the present invention. Any suitable method may be utilized to identify and characterize markers suitable for use in the methods of the present invention. For example, in some embodiments, markers identified as being up or down-regulated in CPPS, e.g. using gene expression microarray methods, are further characterized using tissue microarray, immunohistochemistry, Northern blot analysis, siRNA or antisense RNA inhibition, mutation analysis, investigation of expression with clinical outcome, etc.

In some embodiments, the present invention provides a panel for the analysis of a plurality of markers. The panel allows for the simultaneous analysis of multiple markers correlating with CPPS. For example, a panel may include markers identified as correlating with CPPS Categories I-IV.

Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of CPPS. Such maps can be used for comparison with patient samples. Comparisons can be made utilizing any suitable method, including but not limited to, computer comparison of digitized data. The comparison data is used to provide diagnoses and/or prognoses to patients.

1. Detection of RNA

In some preferred embodiments, CPPS markers (e.g., including but not limited to, those disclosed herein) are detected by measuring the expression of corresponding mRNA in a sample. mRNA expression may be measured by any suitable method (hybridization, amplification, mass, sequencing, etc.).

2. Detection of Protein

In other embodiments, gene expression of CPPS markers is detected by measuring the expression of the corresponding protein or polypeptide. Protein expression may be detected by any suitable method. In some embodiments, proteins are detected by immunohistochemistry or ELISA. In some embodiments, proteins are detected by their binding to an antibody raised against the protein.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a semen, serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine or semen sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., Category III CPPS) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition associated with the disease.

4. Kits

In yet other embodiments, the present invention provides kits for the detection and characterization of prostatic disease. In some embodiments, the kits contain antibodies specific for a CPPS marker, in addition to detection reagents and buffers. In other embodiments, the kits contain reagents specific for the detection of mRNA or cDNA (e.g., oligonucleotide probes or primers). In preferred embodiments, the kits contain all of the components necessary, sufficient, or useful to perform a detection assay, including all controls, directions for performing assays, and any necessary software for analysis and presentation of results.

II. Treatment/Prevention

In some embodiments, the present invention provides compositions and methods for inhibition of mast cell function to treat or prevent CPPS. In some embodiments, the present invention provides compositions and methods for inhibition of CPPS markers to treat or prevent chronic pelvic pain syndrome. In some embodiments, the present invention provides compositions and methods for inhibition of mast cell markers to treat or prevent chronic pelvic pain syndrome. In some embodiments, the present invention provides compositions and methods for inhibition of MCP-1 and/or MIP-1α to treat or prevent chronic pelvic pain syndrome. In some embodiments, the present invention provides compositions and methods for inhibition of MCP-1 to treat or prevent chronic pelvic pain syndrome. In some embodiments, the present invention provides compositions and methods for inhibition of MIP-1α to treat or prevent chronic pelvic pain syndrome. In some embodiments, chronic pelvic pain syndrome is treated or prevented by inhibition of mast cell function and one or more additional therapies (e g inhibition of MCP-1 and MIP-1α). In some embodiments, the present invention provides co-administration of one or more inhibitors of mast cell function and one or more inhibitors of MCP-1 and/or MIP-1α.

In some embodiments, the present invention provides a method of treating, preventing, or ameliorating signs or symptoms of CPPS and/or related or similar diseases, conditions, or disorders in a subject. In some embodiments, compositions and methods of the present invention are provided prophylactically (e.g. to prevent development of CPPS or symptoms thereof). In some embodiments, compositions and methods of the present invention are provided therapeutically (e.g. to treat CPPS or symptoms thereof in a subject suffering from CPPS). In some embodiments, compositions and methods of the present invention provide palliative treatment (e.g. reduction in the symptoms of CPPS). In some embodiments, compositions and methods of the present invention provide curative treatment (e.g. elimination of CPPS in a subject). In some embodiments, compositions and methods of the present invention provide preventative treatment (e.g. prevent the development of CPPS in a subject).

In some embodiments, the present invention provides compositions and methods to treat or prevent CPPS in a subject (e.g. mammal, canine, rodent, primate, human, etc.) via co-administration of one or more inhibitors of mast cell function (e.g. mast cell stabilizer, histamine receptor antagonist, etc.), an inhibitor of one or more CPPS markers (e.g. inhibitor of MCP-1, inhibitor of MIP-1α, etc.). In some embodiments, the present invention provides compositions and methods to treat or prevent CPPS in a subject via co-administration of two or more of: an inhibitor of mast cell function (e.g. mast cell stabilizer, histamine receptor antagonist, etc.), an inhibitor of MCP-1, and an inhibitor of MIP-1α. In some embodiments, the present invention provides one or more of each of: a mast cell stabilizer, a histamine receptor antagonist, an inhibitor of MCP-1, and an inhibitor of MIP-1α. In some embodiments, the present invention provides pharmaceutical compositions comprising a therapeutically effective amount of one or more inhibitors of mast cell function, one or more inhibitors of MCP-1, one or more inhibitors of MIP-1α, and optionally, appropriate pharmaceutically acceptable carriers. In some embodiments, the present invention provides pharmaceutical compositions comprising one or more of a mast cell stabilizer, a histamine receptor antagonist, an inhibitor of MCP-1, and/or an inhibitor of MIP-1α. In some embodiment, the present invention provides co-administration of one or more (e.g. 1, 2, 3, 4, 5, 6, 7, 8, 9, 10, etc.) inhibitors of mast cell function, inhibitors of MCP-1, and/or inhibitors of MIP-1α.

In some embodiments, the present invention provides one or more inhibitors of mast cell function, and methods of use thereof. In some embodiments, an inhibitor of mast cell function inhibits mast cell degranulation. In some embodiments, an inhibitor of mast cell function is a mast cell stabilizer (e.g. cromolyn sodium). In some embodiments, an inhibitor of mast cell function inhibits the release of histamine from mast cells. In some embodiments, an inhibitor of mast cell function is an inhibitor of a histamine receptor (e.g. histamine receptor 1 antagonist (e.g. cetirizine), histamine receptor 2 antagonist (e.g. ranitidine)). In some embodiments, the present invention provides administration of one or more mast cell stabilizers (e.g. cromolyn sodium) and one or more histamine receptor antagonists (e.g. histamine receptor 1 antagonist (e.g. cetirizine), histamine receptor 2 antagonist (e.g. ranitidine)). In some embodiments, the present invention provides administration of one or more mast cell stabilizer (e.g. cromolyn sodium), histamine receptor 1 antagonist (e.g. cetirizine), and/or histamine receptor 2 antagonist (e.g. ranitidine)). In some embodiments, suitable mast cell stabilizers (e.g. inhibitors of degranulation) include, but are not limited to cromolyn sodium, lodoxamide, nedocromil, and derivatives thereof. In some embodiments, suitable histamine receptor 1 antagonists include, but are not limited to: clemastine, diphenhydramine, doxylamine, loratadine, desloratadine, fexofenadine, pheniramine, cetirizine, ebastine, promethazine, chlorpheniramine, levocetirizine, quetiapine, meclizine, dimenhydrinate, and derivatives thereof. In some embodiments, suitable histamine receptor 2 antagonists include, but are not limited to: cimetidine, famotidine, ranitidine, nizatidine, roxatidine, lafutidine, and derivatives thereof.

Where one or more therapeutic agents are to be administered to a subject (e.g., a mast cell stabilizer and a histamine receptor antagonist), the agent may be formulated together and administered simultaneously or may be formulated separately and administered simultaneously or in sequence via any desired timing.

In some embodiments, the present invention provides one or more inhibitors of biomarkers of CPPS (e.g. including but not limited to, MCP-1, MIP-1α, and mast cell tryptase). In some embodiments, the present invention provides one or more inhibitors of MCP-1, MIP-1α, and/or mast cell tryptase. In some embodiments, the present invention provides one or more inhibitors of MCP-1 and/or MIP-1α. In some embodiments, therapies target CPPS markers (e.g., including but not limited to, MCP-1, MIP-1α, mast cell markers (e.g. mast cell tryptase)). Suitable compositions and method of inhibiting CPPS markers (e.g. MCP-1 and/or MIP-1α) are provided in U.S. Pat. App. No. 20050277140, herein incorporated by reference in its entirety. In some embodiments, inhibitors of biomarkers of CPPS (e.g. MCP-1 and/or MIP-1α) include, but are not limited to antisense oligonucleotides, genetic therapies, anti-chemokine therapy, etc.

In some embodiments, the present invention targets the expression of CPPS markers (e.g. by antisense therapy). For example, in some embodiments, the present invention employs compositions comprising oligomeric antisense compounds (e.g., siRNA, miRNA, anti-sense oligonucleotides), particularly oligonucleotides (e.g., those identified in the drug screening methods described above), for use in modulating the function of nucleic acid molecules encoding CPPS markers of the present invention, ultimately modulating the amount of CPPS marker expressed. This is accomplished by providing antisense compounds that specifically hybridize with one or more nucleic acids encoding CPPS markers and interfere with the normal function of the nucleic acid. In some embodiments, expression of CPPS markers is inhibited to treat and/or prevent CPPS and/or symptoms associate therewith. The present invention also includes pharmaceutical compositions and formulations that include the antisense compounds of the present invention as described below.

In some embodiments, the present invention contemplates the use of any genetic manipulation for use in modulating the expression of CPPS markers of the present invention. Examples of genetic manipulation include, but are not limited to, gene knockout (e.g., removing the CPPS marker gene from the chromosome using, for example, recombination), expression of antisense constructs with or without inducible promoters, and the like. Delivery of nucleic acid construct to cells is achieved by any of various methods including, but not limited to, directed injection of naked DNA constructs, bombardment with gold particles loaded with said constructs, and macromolecule mediated gene transfer using, for example, liposomes, biopolymers, and the like.

In some embodiments, the present invention provides compounds which interfere with the production and/or activity of various cytokines (e.g. anti-cytokine compounds), by inhibiting production, processing or activity of a cytokine or its receptor. Thus, the invention also provides a method for treating subjects determined to be suffering from CPPS or other disorders associated with elevated levels of one or more cytokines in one or more components or fractions of semen, preferably seminal plasma, comprising administering one or more anti-cytokine agents, including, but not limited to those disclosed in U.S. Pat. No. 6,180,355.

In some embodiments, the present invention provides treatment and/or prevention of CPPS through administration of two or more therapeutic compounds (e.g. 1, 2, 3, 4, 5, 6 compounds). In some embodiments, the therapeutic compounds are formulated together into a single pharmaceutical composition (e.g. pill, topically-administered liquid, inhalant, etc.). In some embodiments, the therapeutic compounds formulated together within a pharmaceutical composition are configured for separate therapeutic release regimens (e.g. timed release, delayed release, immediate release, etc.). In some embodiments, the therapeutic compounds formulated together within a pharmaceutical composition are configured for immediate effectiveness. In some embodiments, the therapeutic compounds are formulated as separate pharmaceutical compositions to be co-administered. In some embodiments, co-administration comprises administering separate pharmaceutical compositions simultaneously, or near simultaneously. In some embodiments, co-administration comprises a therapeutic strategy in which a subject is administered separate pharmaceutical compositions, but not necessarily together.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

III. Drug Screening

In some embodiments, the present invention provides drug screening assays (e.g., to screen for CPPS drugs). The screening methods of the present invention utilize CPPS markers identified using the methods of the present invention (e.g., including but not limited to, mast cell markers). For example, in some embodiments, the present invention provides methods of screening for compound that directly or indirectly alter (e.g., increase or decrease) the expression of CPPS marker genes.

In one screening method, candidate compounds are evaluated for their ability to alter CPPS marker expression by contacting a compound with a cell expressing a CPPS marker and then assaying for the effect of the candidate compounds on expression. In some embodiments, the effect of candidate compounds on expression of a CPPS marker gene is assayed for by detecting the level of CPPS marker mRNA expressed by the cell. mRNA expression can be detected by any suitable method. In other embodiments, the effect of candidate compounds on expression of CPPS marker genes is assayed by measuring the level of polypeptide encoded by the CPPS markers. The level of polypeptide expressed can be measured using any suitable method, including but not limited to, those disclosed herein.

EXPERIMENTAL

The following examples are provided in order to demonstrate and further illustrate certain preferred embodiments and aspects of the present invention and are not to be construed as limiting the scope thereof.

Example 1

Treating Chronic Pelvic Pain Syndrome

The experimental autoimmune prostatitis (EAP) model was selected for experiments conducted during development of embodiments of the present invention. Autoimmunity is one of the etiologies for patients with CPPS. Rat prostate antigen instillation in NOD mice provokes a chronic inflammation that is multifocal and evenly distributed in all the prostatic lobes. Pelvic pain was examined in NOD and C57BL/6 (B6) mice using quantitative behavior testing methods to assess tactile sensitivity of the suprapubic region. Mechanical stimulation of the pelvic area of sham-immunized mice with Von Frey fibers resulted in a response frequency that correlated with the applied force, and this response profile did not change during the 30-day course of the experiment (SEE FIG. 1). In contrast, EAP induced NOD mice exhibited enhanced sensitivity to pelvic stimuli that was significantly greater at all filaments by post-immunization day 10 in NOD mice (SEE FIG. 1) and was sustained through the end of the experiment on day 30. When expressed as increase in pain from baseline there was an approximately 350% increase in pain behavior compared to sham controls (SEE FIG. 1). This indicates the development of chronic pelvic pain in EAP mice and is the first report of chronic pain symptoms in an animal model of prostatitis.

Figure 2:
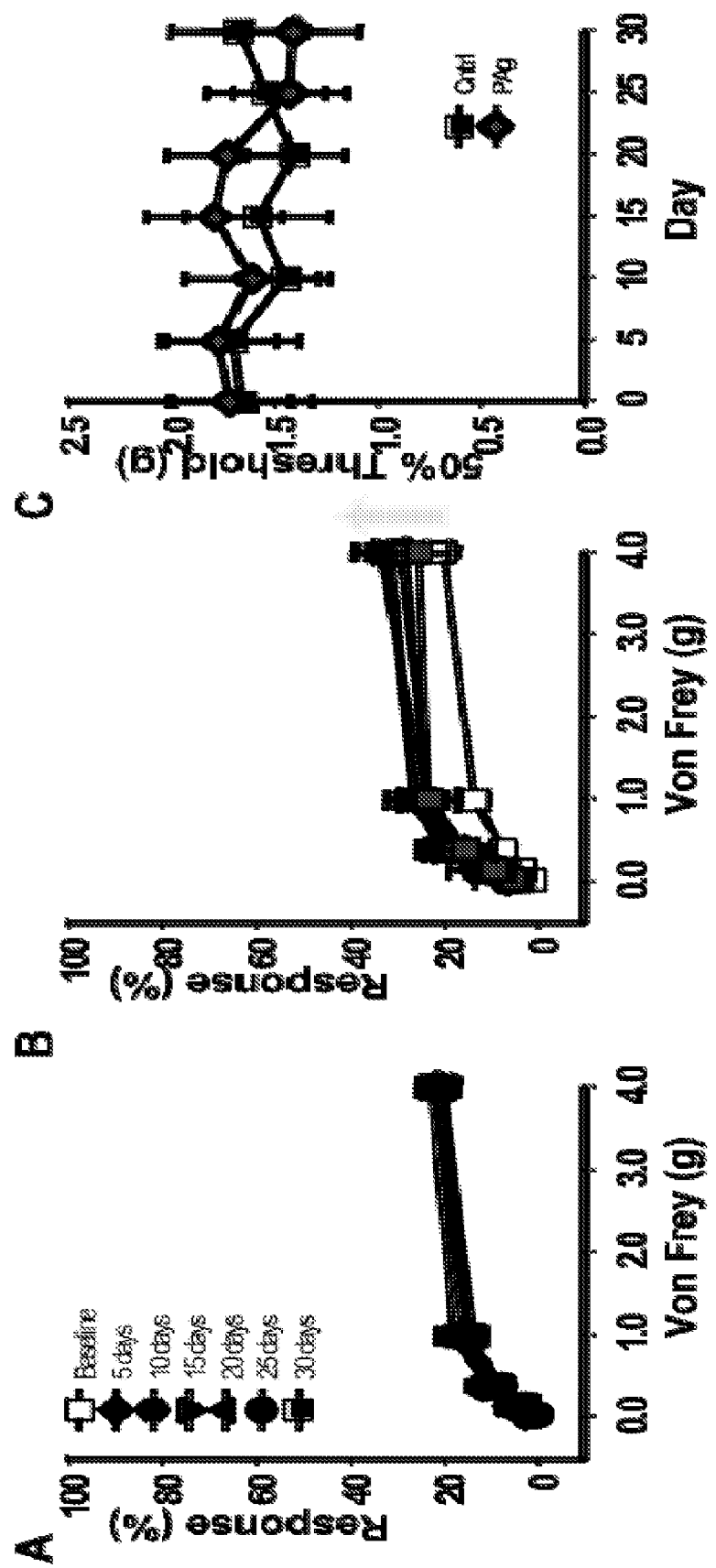
FIG. 2 shows EAP induces chronic pelvic pain in male B6 mice. Tactile allodynia was measured as responses to mechanical stimulation of the pelvic region and hind paw using von Frey filaments of 5 calibrated forces. A) Responses to pelvic stimulation of sham-injected male B6 mice receiving injection Titer Max. B) Responses to pelvic stimulation of male B6 mice injected with PAg. ANOVA indicated an increase in response frequency from baseline at all filaments tested in PAg-treated mice at days 15-20 with no significant differences in baseline between controls and PAg treated mice. C) PAg induced no significant change in tactile sensitivity (50% threshold) of the plantar region of the paw.

Experiments were conducted during development of embodiments of the present invention to determine whether chronic pain development was mouse strain specific by using wild-type C57BL/6 (B6) mice. In EAP-induced B6 mice, sensitivity was increased to mechanical stimulation but to a lesser magnitude (SEE FIG. 2B). EAP induced no changes in tactile sensitivity of the plantar region of the hind paw (SEE FIG. 2C). Therefore, EAP induces chronic pain specific to the pelvic region in both NOD and B6 mice. To confirm that the effects of prostate antigen (PAg) were specific to pain behavior, normal behaviors during free roaming were quantified in both mouse strains. PAg induced no significant differences in grooming, cage crossing, or rearing, suggesting that pelvic pain is evoked and not due to spontaneous pain. There was also no prolonged change in weight indicating that PAg is not associated with dramatic changes in gross physiology. Thus, pain specific to the suprapubic area can be recreated in a murine model through EAP and persists in a chronic fashion without any gross systemic effects on the animal. The EAP model represents a chronic model which transitions from a focus on prostatitis etiology to one on the symptoms of the disease. The model closely reflects CPPS, a syndrome that has uncertain etiology and is diagnosed based on symptoms.

Figure 3:
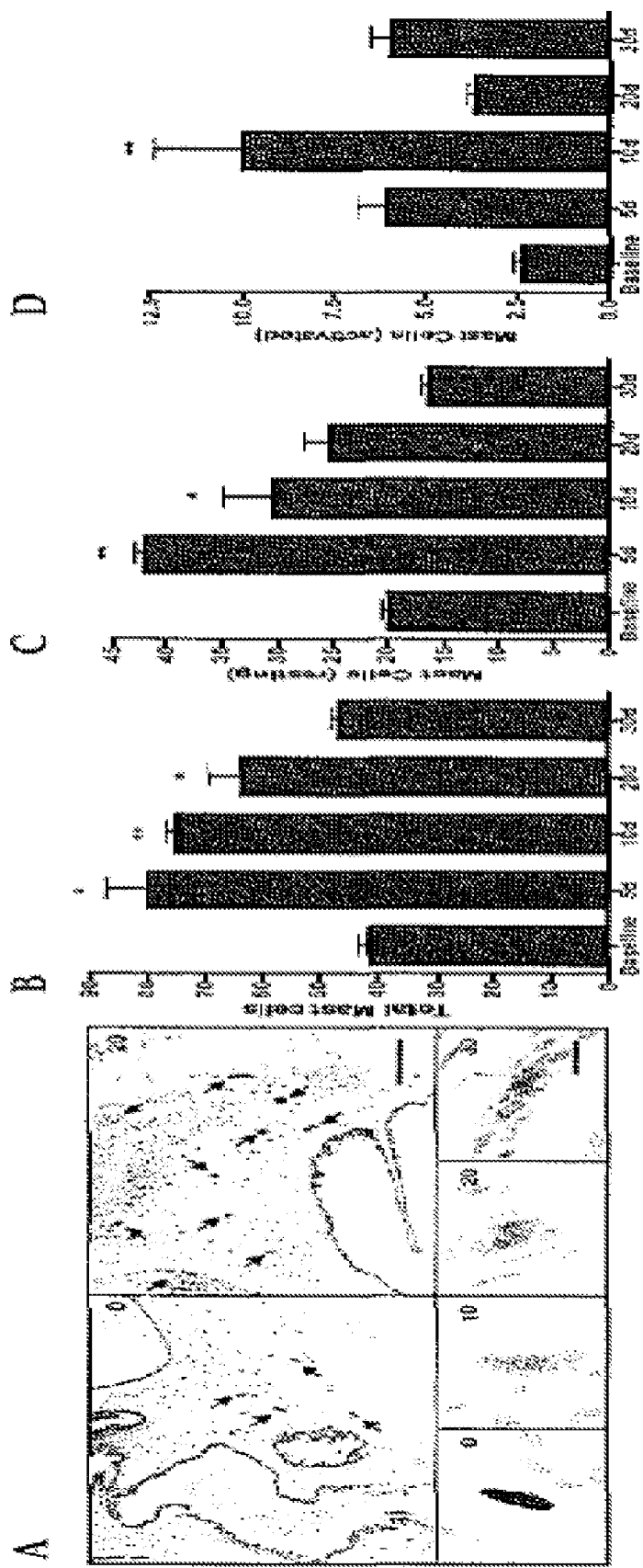
FIG. 3 shows mast cell recruitment and activation are observed in the prostates of EAP mice. NOD mouse prostate sections were stained with the acidified toluidine blue and total mast cells, resting mast cells, and activated mast cells were quantified in a blinded fashion. Before induction of EAP, few mast cells that were largely resting (A. see arrows and t=0) were observed. At 10, 20 and 30 days after induction larger number of mast cells of an activated phenotype were observed (see T=10, 20 and 30). Total mast cell numbers were increased till 20 days (B), with significant majority of cells being of the resting phenotype at 5 and 10 days (C). Activated cells were observed to be maximal at 10 days followed by a reduction in detection.

Mast cell tryptase has been used in a variety of human disease conditions as a biomarker for total mast cell number and activation. Experiments conducted during development of embodiments of the present invention, using an autoimmune murine model that recapitulates aspects of CPPS including the presence of chronic pelvic pain, demonstrated a significant increase in total and activated mast cells in the prostates of mice with pelvic pain. Prostates from mice were examined for total mast cell numbers as well as activation status of the mast cells. Mast cells were classified as resting, partially activated or activated depending on the dispersal of toluidine stained granules. Resting mast cells contained greater than 90% of visible granules in the cell boundary. Partially active mast cells showed approximately 10% to 20% of visible granules beyond the cell boundary. Activated mast cells demonstrated greater than 20% of visible granules beyond the cell boundary, while granule dispersion was typically greater than 50% in active cells. Total mast cells were observed to be increased 5 days after induction of EAP with majority of cells in the resting stage. By day 10 there was significant activation of mast cells that was not observed at 20 and 30 days (SEE FIG. 3). However, the apparent reduction in resting cells at 20 and 30 days with the absence of any increase in activated cells suggests that some late stage activated cells are not detected by toluidine blue staining Thus EAP causes significant increase in mast cell numbers and results in mast cell activation at time points that also correspond to elevated pain symptoms.

Figure 4:
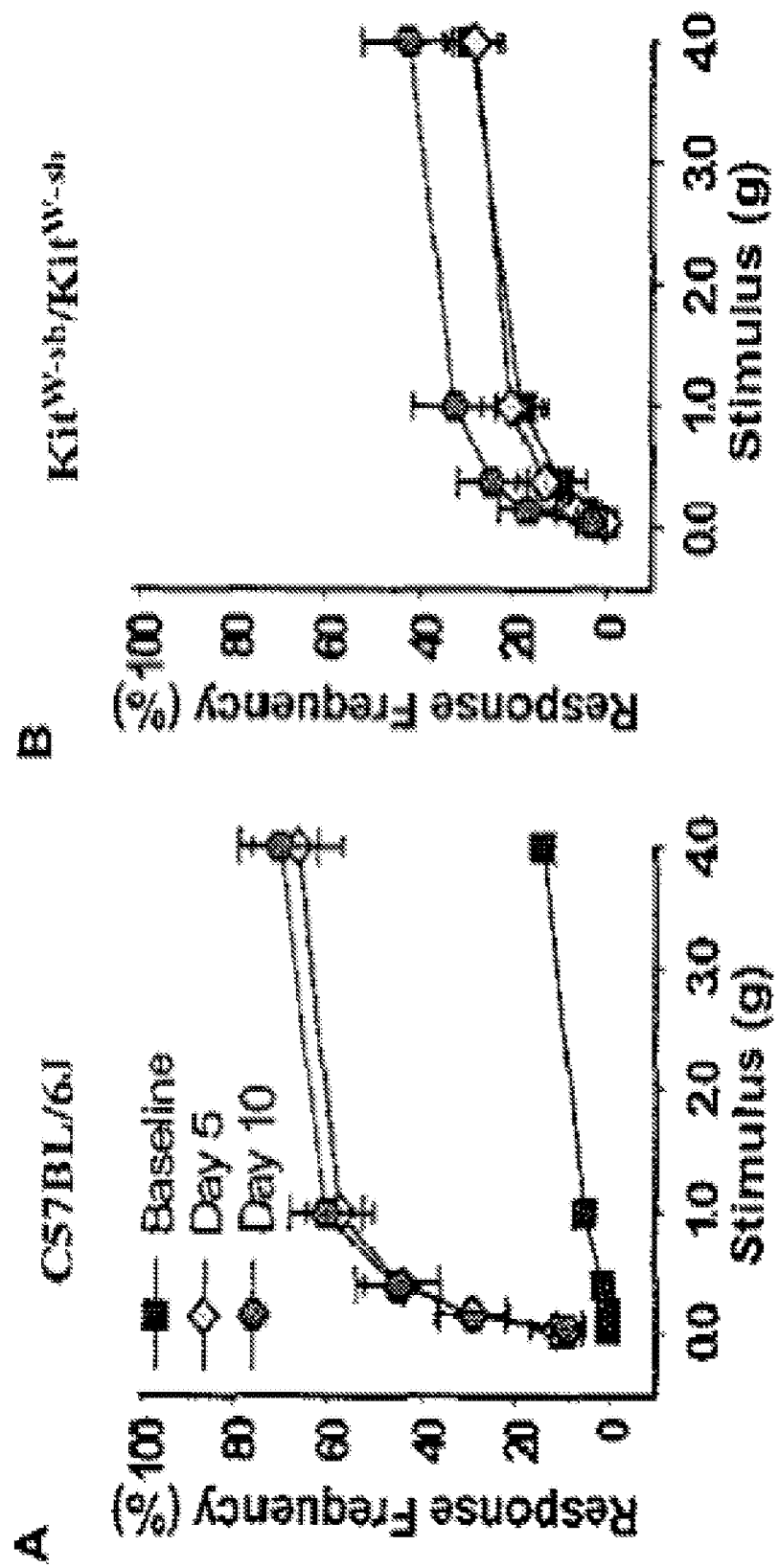
FIG. 4 shows pelvic pain behavior in wild type (C57BLJ6J) and mast cell deficient mice.

The requirement for mast cell deficient mice to mediate pain in the animal model was confirmed by examining the ability of mast cell deficient mice ($Kit^{W-sh}/Kit^{W-sh}$) to exhibit tactile allodynia of the pelvic region upon induction of autoimmune prostatitis. Wild-type C57BL/6 mice developed robust pelvic pain behavior by day 5 after antigen administration that persisted at day 10 (SEE FIG. 4A). In contrast, $Kit^{W-sh}/Kit^{W-sh}$ mice did not show any increase in pelvic pain behavior at 5 days and showed inhibited pain responses at 10 days after antigen administration (SEE FIG. 4B). In addition, both groups of mice exhibited no changes in pain responses in the footpad or significant changes in body weight. These data indicate that mast cells are involved in the development of pelvic pain behavior.

Figure 5:
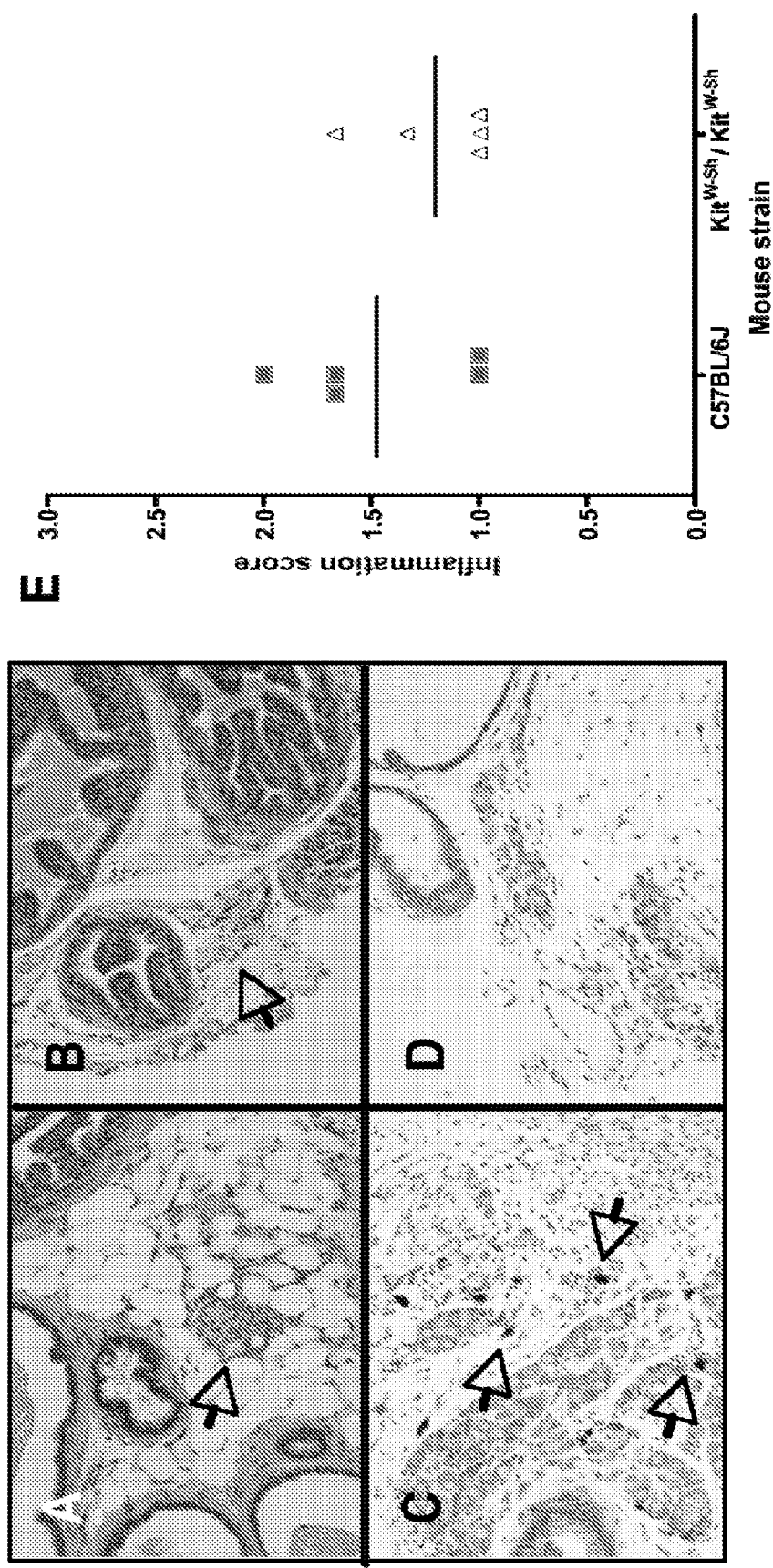
FIG. 5 shows EAP in mast cell deficient (KitW$^{-sh}$/KitW$^{-sh}$) mice is associated with chronic inflammation.

Experiments conducted during development of embodiments of the present invention demonstrated that mast cell deficient mice and wild-type mice develop similar levels of EAP-induced chronic inflammation. The extent of chronic inflammation in mast cell deficient mice ($Kit^{W-sh}/Kit^{W-sh}$) was compared to wild-type C57BL/6 mice upon induction of autoimmune prostatitis. Inflammation in both groups of mice was chronic with multiple foci of inflammatory cells distributed predominantly in the periglandular regions and stroma of the prostate (SEE FIGS. 5A and 5B). Both groups of mice developed chronic inflammation that was not statistically different when quantified using standard inflammation scoring (SEE FIG. 5E). In contrast, toluidine blue staining for mast cells revealed large numbers of mast cells in various stages of activation in the stroma of C57BL/6 but not $Kit^{W-sh}/Kit^{W-sh}$ mice (see arrows SEE FIGS. 5C and 5D). Thus, mast cells are not a requirement for the development of inflammation, but have a critical role for the establishment of chronic pain.

Figure 6:
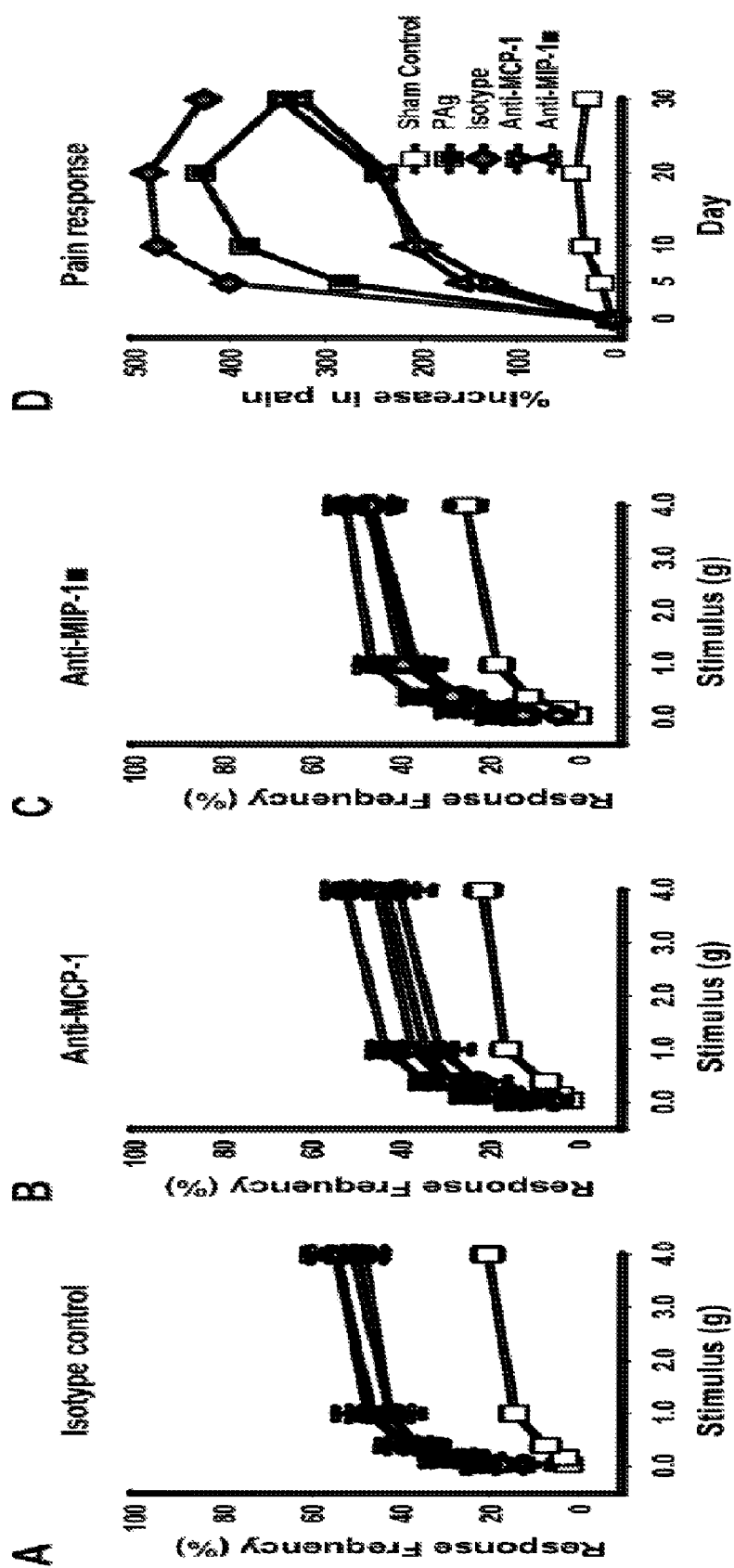
FIG. 6 shows Anti-MCP-1 or Anti-MIP-la antibodies reduce pain development in EAP.
Figure 7:
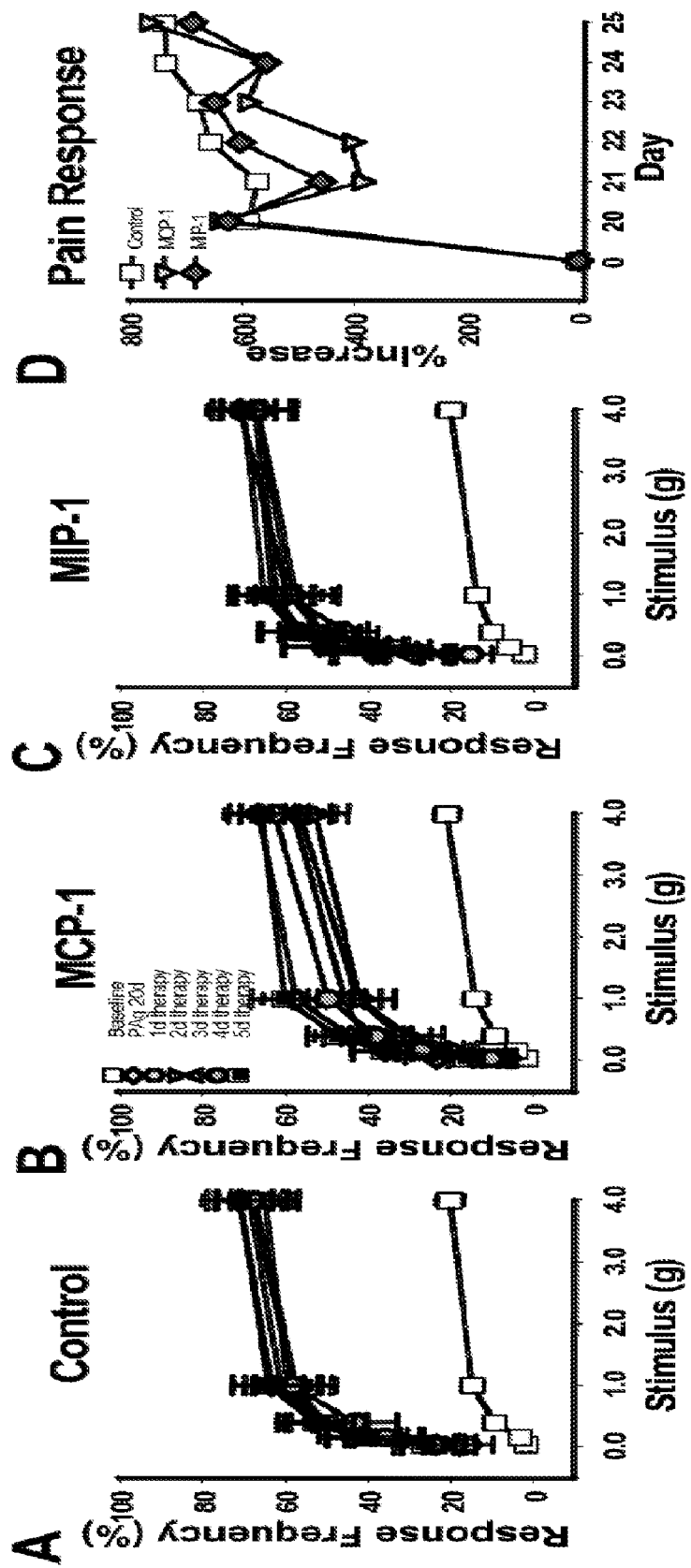
FIG. 7 shows Anti-MCP-1 antibody therapy reduces pain in EAP.

Experiments conducted during development of embodiments of the present invention demonstrated that anti-MCP-1 or anti-MIP-1α antibodies reduce pelvic pain development. Experiments were conducted to examine whether anti-MCP-1 therapy could be used to inhibit the development of pelvic pain in the animal model. Commercially derived (R&D systems) polyclonal anti-MCP-1, anti-MIP-1α and an isotype control antibody were used to examine their ability to prevent the development of pelvic pain. Antibodies were administered to NOD mice at the time of initiation of autoimmunity and pain was evaluated at 5, 10, 20 and 30 days post injection. A significant decrease of 68% was observed in pain responses using the anti-MCP-1 (SEE FIG. 6B), 61% using the anti-MIP-1α (SEE FIG. 6C) and no reduction in pain using the control antibody (SEE FIG. 7) at 5, 10 and 20 days after antibody administration. Pain responses returned to pre-antibody administration levels by 30 days suggesting that the inhibitory action of the antibody was no longer retained. These data demonstrate that pelvic pain in this model of CP/CPPS can be inhibited using antibodies targeting MCP-1 and MIP-1α. These results indicate that anti-MCP-1 or anti-MIP-1α are therapeutic targets that reduce pelvic pain in CPPS. Therapeutic use of these antibodies to reduce pain after it had developed in the EAP model was examined (SEE FIG. 7). Antibodies were administered at 20 days after EAP induction based on our earlier results indicating peak expression at 20 days. Anti-MCP-1 was able to significantly reduce pain for up to 2 days following treatment after which time pain returned to control levels. Anti-MIP-1 alpha antibodies showed a reduction in pain symptoms that was, however, not statistically significant. These results indicate that chemokine inhibition is a viable therapeutic mechanism to reduce pelvic pain symptoms.

Figure 8:
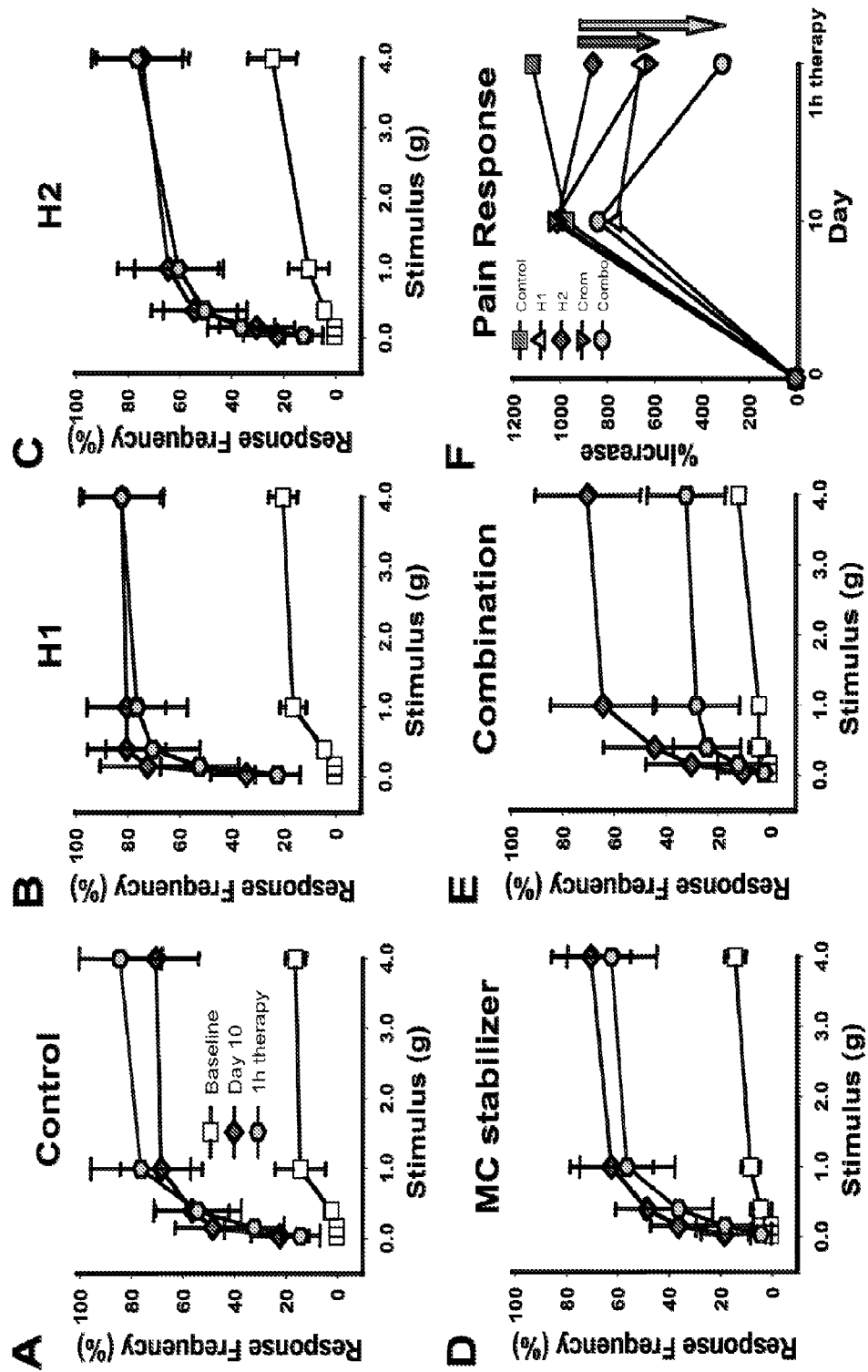
FIG. 8 shows functional inhibitors of mast cell products or mast cell degranulation therapeutically reduce pelvic pain in EAP. Mice injected with rat prostate antigen (PAg) were tested at baseline and 10 days after injection for the development of pain behavior. Mice were treated at day 10 by intraperitoneal injection with saline (Control, A), 10 mg/kg each of cetrizine (H1, B), ranitidine (H2, C), Cromolyn sodium (MC stabilizer, D) or all three drugs (Combination, E) in a 200 µl volume. Following blinding of treatment and control groups, pelvic pain behavior was tested one hour after drug administration.
Figure 9:
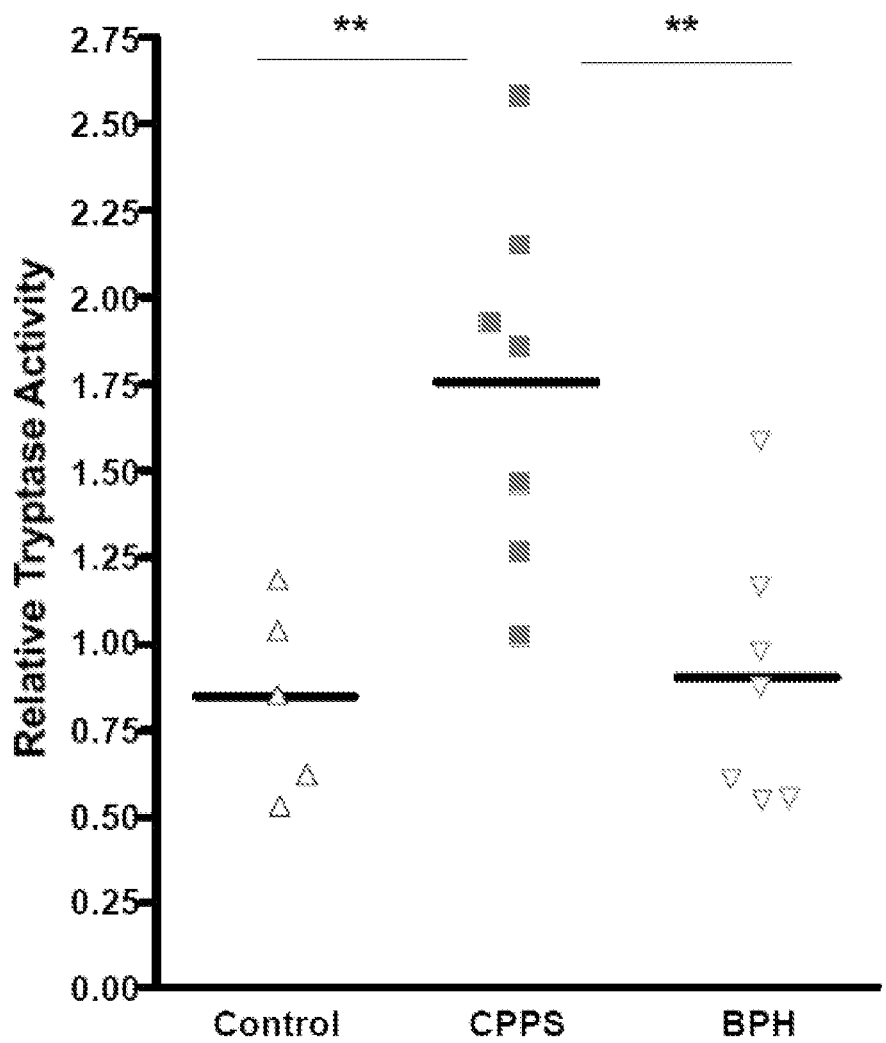
FIG. 9 shows mast cell tryptase was significantly elevated in EPS from CPPS but not in BPH. Samples were normalized (200 ug) for protein concentration and tryptase activity was calculated relative to a positive standard.
Figure 10:
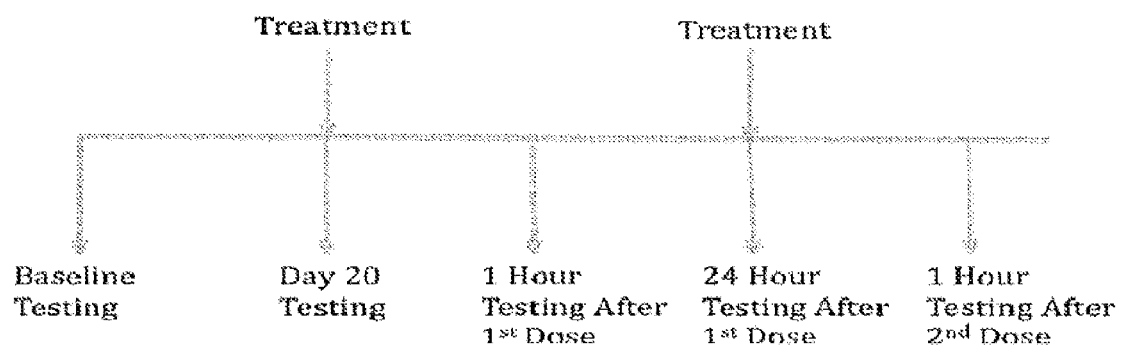
FIG. 10 shows an exemplary experimental design to assess the efficacy of mast cell inhibitors on chronic pelvic pain. EAP induction occurred for 20 days in NOD mice. Pain was assessed at the baseline, 20 days, 1 hour post treatment, 24 hours post treatment, and 1 hour post second treatment.

Experiments conducted during development of embodiments of the present invention demonstrated that pharmacological inhibitors of mast cell function therapeutically reduce pelvic pain behavior in mice. Pelvic pain behavior in the EAP model was inhibited following the establishment of pain. EAP was induced in NOD mice and pelvic pain behavior at baseline and 10 days after disease onset was measured. Mice were administered a mast cell stabilizer, cromolyn sodium; a histamine receptor 1 antagonist, cetirizine; a histamine receptor 2 antagonist, ranitidine; and a combination of all three pharmacological agents or saline as control. Pelvic pain behavior was tested one hour after drug administration. Results indicate that treatment with the combination of all three pharmacological agents reduced pain behavior by 64% (SEE FIGS. 8E and 8F) while treatment with cromolyn sodium alone reduced pain by 39.6% (SEE FIGS. 8D and 8F). In contrast, treatment with H1 and H2 receptor antagonists reduced pain behavior by 13.6% and 15.9% respectively while controls exhibited no reduction in pain behavior. These results clearly indicate that mast cells and their granule contents play an important role in the continued presence of pelvic pain in the EAP animal model. These data also indicate that therapeutic intervention in established chronic pelvic pain may be achieved by selective targeting of mechanisms of mast cell activation and degranulation.

Experiments conducted during development of embodiments of the present invention demonstrate that pelvic pain behavior is inhibited by targeting MCP-1 and MIP-1α, as well as inhibitors of mast cell degranulation and function. These studies indicate that therapeutic strategies that are multimodal and inhibit multiple actors in the pathogenesis of pelvic pain are effective in the treatment of CPPS.

Example 2

Mast Cell Tryptase is a Biomarker for CPPS

Mast cell tryptase has been used in a variety of human disease conditions as a biomarker for total mast cell number and activation. Experiments conducted during development of embodiments of the present invention, using an autoimmune murine model that recapitulates aspects of CPPS including the presence of chronic pelvic pain, demonstrated a significant increase in total and activated mast cells in the prostates of mice with pelvic pain. Prostates from mice were examined for total mast cell numbers as well as activation status of the mast cells. Mast cells were classified as resting, partially activated or activated depending on the dispersal of toluidine stained granules. Resting mast cells contained greater than 90% of visible granules in the cell boundary. Partially active mast cells showed approximately 10% to 20% of visible granules beyond the cell boundary. Activated mast cells demonstrated greater than 20% of visible granules beyond the cell boundary, while granule dispersion was typically greater than 50% in active cells. Total mast cells were observed to be increased 5 days after induction of EAP with majority of cells in the resting stage. By day 10 there was significant activation of mast cells that was not observed at 20 and 30 days (SEE FIG. 3). However, the apparent reduction in resting cells at 20 and 30 days with the absence of any increase in activated cells suggests that some late stage activated cells are not detected by toluidine blue staining Thus EAP causes significant increase in mast cell numbers and results in mast cell activation at time points that also correspond to elevated pain symptoms.

The requirement for mast cell deficient mice to mediate pain in the animal model was confirmed by examining the ability of mast cell deficient mice ($Kit^{W-sh}/Kit^{W-sh}$) to exhibit tactile allodynia of the pelvic region upon induction of autoimmune prostatitis. Wild-type C57BL/6 mice developed robust pelvic pain behavior by day 5 after antigen administration that persisted at day 10 (SEE FIG. 4A). In contrast, $Kit^{W-sh}/Kit^{W-sh}$ mice did not show any increase in pelvic pain behavior at 5 days and showed inhibited pain responses at 10 days after antigen administration (SEE FIG. 4B). In addition, both groups of mice exhibited no changes in pain responses in the footpad or significant changes in body weight. These data indicate that mast cells are involved in the development of pelvic pain behavior.

Experiments conducted during development of embodiments of the present invention using clinical samples of expressed prostatic fluid (EPS) from patients with CPPS IIIb, benign prostatic hypertrophy (BPH), and control subjects demonstrate that mast cell tryptase provides a biomarker for CPPS (e.g. for diagnosis and/or characterization of CPPS). The presence of mast cell tryptase was measured using a colorimetric substrate based assay (Millipore) as an index of mast cell degranulation. EPS samples from CPPS patients demonstrated a significant increase in tryptase levels when compared to controls or BPH patient samples (SEE FIG. 3). In contrast, BPH samples did not show a significant increase in tryptase expression from controls (SEE FIG. 3). These data indicate that mast cell tryptase provides a biomarker for identification, detection, and/or characterization of CPPS in humans. These data indicate that mast cells and their degranulation products play a role in CPPS pathogenesis.

Example 3

Synergism, Dosing, and Administration

Figure 12:
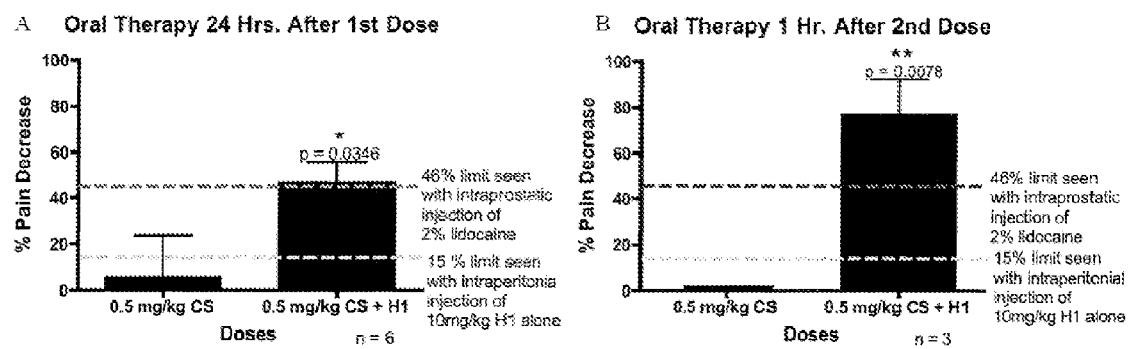
FIG. 12 shows histograms demonstrating the decrease in pain resulting from oral administration at the 24 hour time point and the 1 hour time point after the second treatment are the time points in which significant pain reduction was found for the oral therapy. The absence of a bar in panel B indicates a pain increase. Pain reduction was compared to intraporstatic lidocaine which is current standard of care and with Cetirizine alone (dotted horizontal lines).
Figure 13:
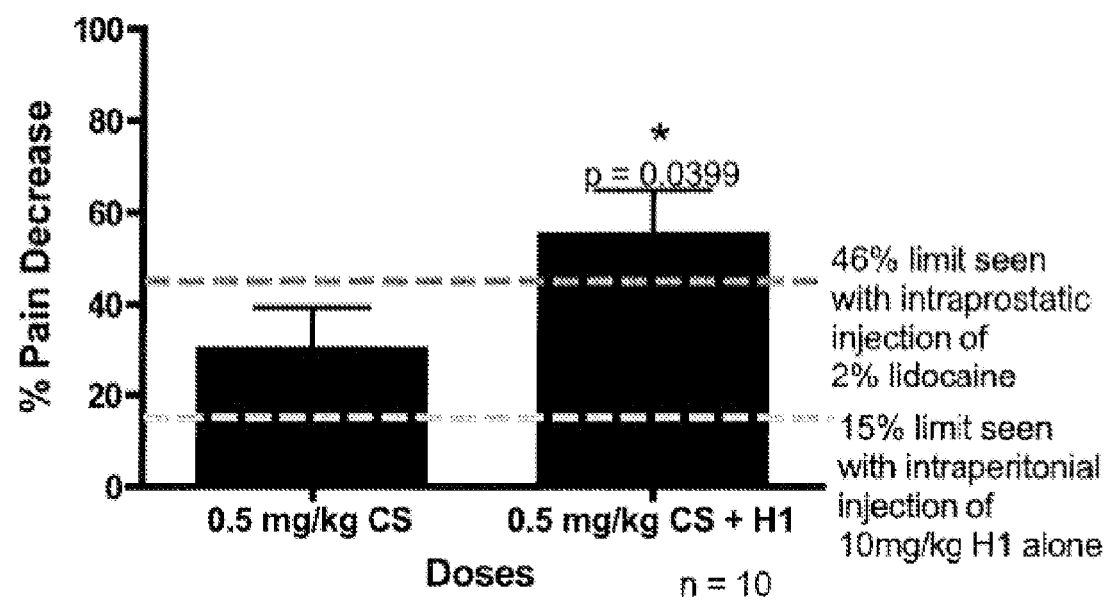
FIG. 13 shows a histogram demonstrating the decrease in pain resulting from intraperitoneal administration of cromolyn sodium alone or in combination with Cetirizine (H1) at the 24 hour time point. Pain reduction was compared to intraporstatic lidocaine which is current standard of care and with Cetirizine alone (dotted horizontal lines).
Figure 14:
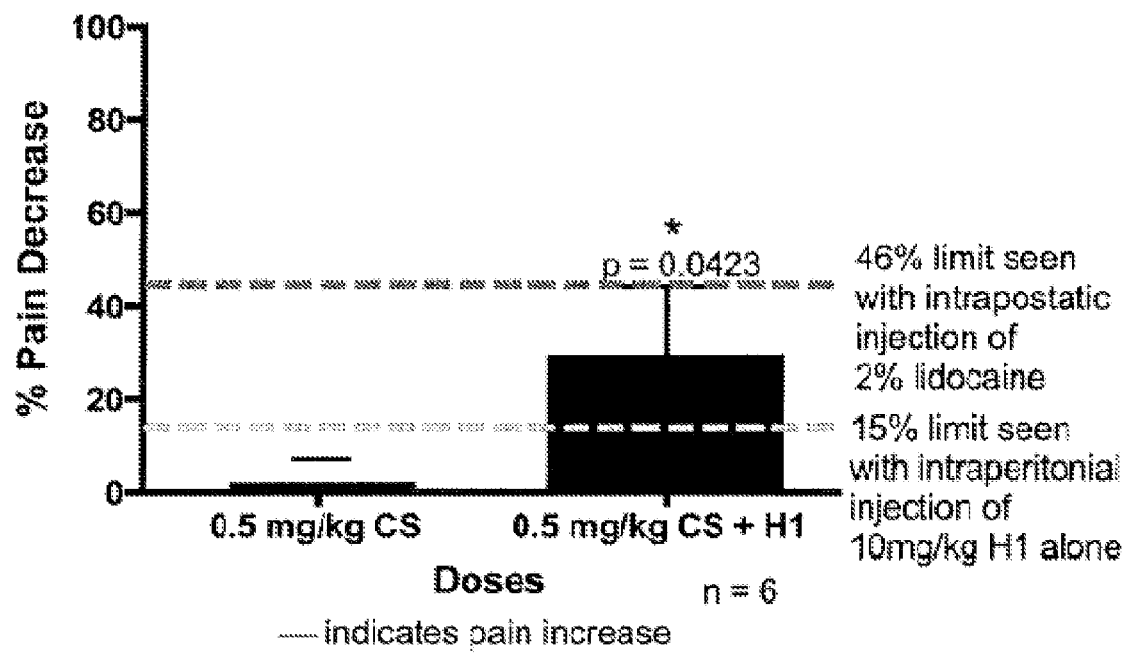
FIG. 14 shows a histogram demonstrating the decrease in pain resulting from intravenous administration of cromolyn sodium alone or in combination with Cetirizine (H1) at the 24 hour time point. Pain reduction was compared to intraporstatic lidocaine which is current standard of care and with Cetirizine alone (dotted horizontal lines).

Experiments were conducted to: (1) identify synergism between a mast cell inhibitor (cromolyn sodium) and a histamine 1 receptor antagonist (cetirizine), (2) identify optimized dose of cromolyn sodium that exhibits synergism with a fixed dose of cetirizine, and (3) identify the optimized route of administration for the combination therapy (SEE FIG. 11). The results indicated that the combination treatment of CS and Cetrizine is significantly more effective than CS alone in reducing pelvic pain in EAP mice. Synergism is assumed when the dose of combination producing a 50% effect is less than the dose from the 50% effect produced by a pure ly additive mixture of the two components of the combination. Intraprostatic lidocaine was utilized as the standard for maximal pain benefit. The 24 hour time point and the 1 hour time point after the second treatment are the time point s in which significant pain reduction was found for the oral therapy. Oral (SEE FIG. 12), intraperitoneal (SEE FIG. 13), and intravenous (SEE FIG. 14) administration was tested.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for treating chronic pelvic pain syndrome in a subject, comprising administering to said subject a therapeutically effective amount of:
   (a) a mast cell stabilizer;
   (b) a combination of:
      (i) a mast cell stabilizer and
      (ii) a histamine receptor 1 antagonist and/or a histamine receptor 2 antagonist; or
   (3) a combination of:
      (i) a mast cell stabilizer,
      (ii) a histamine receptor 1 antagonist and/or a histamine receptor 2 antagonist, and
      (iii) an inhibitor of MCP-1 or MIP-1α, wherein the inhibitor is an antibody which binds MCP-1 or MIP-1α.

2. The method of claim 1, wherein said subject is administered a mast cell stabilizer, but is not administered a histamine receptor 1 antagonist and/or histamine receptor 2 antagonist.

3. The method of claim 1, wherein said subject is administered a combination of a mast cell stabilizer and a histamine receptor 1 antagonist and/or a histamine receptor 2 antagonist.

4. The method of claim 3, wherein said subject is further administered an inhibitor of MCP-1 and/or MIP-1α, wherein the inhibitor is an antibody which binds MCP-1 or MIP-1α.

5. The method of claim 3, wherein said histamine receptor 1 antagonist and/or histamine receptor 2 antagonist is a histamine receptor 1 antagonist.

6. The method of claim 5, further comprising administering an inhibitor of MCP-1 or MIP-1α, wherein the inhibitor is an antibody which binds MCP-1 or MIP-1α.

7. The method of claim 3, wherein said histamine receptor 1 antagonist and/or histamine receptor 2 antagonist is a histamine receptor 2 antagonist.

8. The method of claim 7, further comprising administering an inhibitor of MCP-1 or MIP-1α, wherein the inhibitor is an antibody which binds MCP-1 or MIP-1α.

9. The method of claim 3, wherein said subject is not administered an antibody which binds MCP-1 or MIP-1α.

\* \* \* \* \*

UNITED STATES PATENT AND TRADEMARK OFFICE
CERTIFICATE OF CORRECTION

PATENT NO. : 8,586,044 B2
APPLICATION NO. : 13/118156
DATED : November 19, 2013
INVENTOR(S) : Praveen Thumbikat et al.

Page 1 of 1

It is certified that error appears in the above-identified patent and that said Letters Patent is hereby corrected as shown below:

IN THE SPECIFICATION:

Column 1, Lines 13-17 reads: "This invention was made with government support under Grant No. 1K01DK079019-01A2 awarded by the National Institutes of Health, National Institute of Diabetes and Digestive and Kidney Diseases. The government has certain rights in the invention."

HOWEVER, IT SHOULD READ:

Column 1, Lines 13-17: "This invention was made with government support under 1 K01 DK079019 awarded by the National Institutes of Health. The government has certain rights in the invention."

IN THE CLAIMS:

CLAIM 1 reads: "...(3) a combination of:
(i) a mast cell stabilizer,
(ii) a histamine receptor 1 antagonist and/or a histamine receptor 2 antagonist, and
(iii) an inhibitor of MCP-1 or MIP-1 α, wherein the inhibitor is an antibody which binds MCP-1 or MIP-1 α."

HOWEVER, IT SHOULD READ:

CLAIM 1: "... (c) a combination of:
(i) a mast cell stabilizer,
(ii) a histamine receptor 1 antagonist and/or a histamine receptor 2 antagonist, and
(iii) an inhibitor of MCP-1 or MIP-1 α, wherein the inhibitor is an antibody which binds MCP-1 or MIP-1 α."

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,586,044 B2
APPLICATION NO. : 13/118156
DATED : November 19, 2013
INVENTOR(S) : Praveen Thumbikat et al.

It is certified that error appears in the above-identified patent and that said Letters Patent is hereby corrected as shown below:

IN THE SPECIFICATION:

Column 1, Lines 13-17 reads: "This invention was made with government support under Grant No. 1K01DK079019-01A2 awarded by the National Institutes of Health, National Institute of Diabetes and Digestive and Kidney Diseases. The government has certain rights in the invention."

HOWEVER, IT SHOULD READ:

Column 1, Lines 13-17: "This invention was made with government support under 1 K01 DK079019 awarded by the National Institutes of Health. The government has certain rights in the invention."

IN THE CLAIMS:

Column 24, line 38, CLAIM 1 reads: "...(3) a combination of:
(i) a mast cell stabilizer,
(ii) a histamine receptor 1 antagonist and/or a histamine receptor 2 antagonist, and
(iii) an inhibitor of MCP-1 or MIP-1α, wherein the inhibitor is an antibody which binds MCP-1 or MIP-1α."

HOWEVER, IT SHOULD READ:

Column 24, line 38, CLAIM 1: "... (c) a combination of:
(i) a mast cell stabilizer,
(ii) a histamine receptor 1 antagonist and/or a histamine receptor 2 antagonist, and
(iii) an inhibitor of MCP-1 or MIP-1α, wherein the inhibitor is an antibody which binds MCP-1 or MIP-1α."

This certificate supersedes the Certificate of Correction issued February 18, 2014.

Signed and Sealed this
Twenty-fifth Day of March, 2014

Michelle K. Lee
*Deputy Director of the United States Patent and Trademark Office*